(12) United States Patent
Kim et al.

(10) Patent No.: US 11,464,398 B2
(45) Date of Patent: Oct. 11, 2022

(54) CAPSULE-TYPE ENDOSCOPE FOR RECEIVING CONTROL SIGNAL USING LIGHT SOURCE DRIVING POWER LINE AND METHOD OF CONTROLLING CAPSULE-TYPE ENDOSCOPE

(71) Applicant: Industry-Academic Cooperation Foundation, Chosun University, Gwangju (KR)

(72) Inventors: Youn Tae Kim, Daejeon (KR); Si Ho Shin, Gwangju (KR); Jae Hyo Jung, Gwangju (KR)

(73) Assignee: Industry-Academic Cooperation Foundation, Chosun University, Gwanju (KR)

( * ) Notice: Subject to any disclaimer, the term of this patent is extended or adjusted under 35 U.S.C. 154(b) by 0 days.

(21) Appl. No.: 17/135,090

(22) Filed: Dec. 28, 2020

(65) Prior Publication Data
US 2022/0151471 A1     May 19, 2022

(30) Foreign Application Priority Data
Nov. 16, 2020 (KR) .................. 10-2020-0152726

(51) Int. Cl.
| A61B 1/04 | (2006.01) |
| A61B 1/00 | (2006.01) |
| H04N 5/235 | (2006.01) |
| A61B 1/06 | (2006.01) |
| H04N 5/225 | (2006.01) |

(52) U.S. Cl.
CPC ...... *A61B 1/00158* (2013.01); *A61B 1/00006* (2013.01); *A61B 1/00016* (2013.01); *A61B 1/00032* (2013.01); *A61B 1/041* (2013.01); *A61B 1/06* (2013.01); *H04N 5/2354* (2013.01); *H04N 2005/2255* (2013.01)

(58) Field of Classification Search
CPC ............ A61B 1/00158; A61B 1/00006; A61B 1/00016; A61B 1/00032; A61B 1/041; A61B 1/06; H04N 5/2354; H04N 2005/2255
See application file for complete search history.

(56) References Cited

U.S. PATENT DOCUMENTS

| 10,045,713 | B2* | 8/2018 | Old ........................ G16Z 99/00 |
| 2005/0064815 | A1* | 3/2005 | Kanazawa ............ A61B 1/041 455/41.1 |
| 2005/0143649 | A1* | 6/2005 | Minai .................... A61B 5/062 600/410 |
| 2006/0152309 | A1* | 7/2006 | Mintchev ............... H02N 15/00 335/58 |
| 2007/0066868 | A1* | 3/2007 | Shikii .................... A61B 5/073 600/118 |
| 2008/0249360 | A1 | 10/2008 | Li et al. |

(Continued)

*Primary Examiner* — Howard D Brown, Jr.
(74) *Attorney, Agent, or Firm* — Renner, Otto, Boisselle & Sklar, LLP (57) ABSTRACT

A capsule-type endoscope including a battery, a camera configured to capture internal organ images, a light source configured to irradiate light to capture the internal organ images, and a light source driving power line supplying power, stored in the battery, to the light source. The light source driving power line is a loop antenna coil for reception of a control signal from an external coupled loop antenna coil for transmission.

5 Claims, 5 Drawing Sheets

(56) References Cited

U.S. PATENT DOCUMENTS

| | | | | |
|---|---|---|---|---|
| 2009/0054731 A1* | 2/2009 | Shigemori | ............ | A61B 5/073 600/118 |
| 2013/0225981 A1* | 8/2013 | Hasegawa | ............ | A61B 5/061 600/424 |
| 2014/0163357 A1* | 6/2014 | Higaki | ............ | G01S 5/14 600/424 |
| 2017/0367561 A1* | 12/2017 | Park | ............ | A61B 1/00009 |
| 2018/0235449 A1* | 8/2018 | Kim | ............ | A61B 1/041 |
| 2021/0184712 A1* | 6/2021 | Kim | ............ | H04B 13/005 |

* cited by examiner

CAPSULE-TYPE ENDOSCOPE FOR RECEIVING CONTROL SIGNAL USING LIGHT SOURCE DRIVING POWER LINE AND METHOD OF CONTROLLING CAPSULE-TYPE ENDOSCOPE

CROSS-REFERENCE TO RELATED APPLICATION(S)

This application claims the benefit under 35 USC 119 (a) of Korean Patent Application No. 10-2020-0152726 filed on Nov. 16, 2020 in the Korean Intellectual Property Office, the entire disclosure of which is incorporated herein by reference for all purposes.

BACKGROUND

1. Field

The present disclosure relates to a capsule-type endoscope for receiving a control signal using a light source driving power line.

2. Description of the Background

Capsule-type endoscopes are medical devices used to examine the internal organs of the body. In a case in which patients swallow capsule-type endoscopes like a pill, capsule-type endoscopes move from the oral cavity to the rectum, while capturing images of internal organs, such as the stomach, the small intestine, and the large intestine, and may be excreted from the human body.

Images captured by a camera provided in capsule-type endoscopes are wirelessly transmitted to an image storage device worn on the body of a patient. The images transmitted during an inspection period may be continuously stored in an image storage device. After the inspection is completed, doctors may use the images stored in the image storage device to diagnose the health condition of patients. In terms of the use of capsule-type endoscopes, there is none of the pain and discomfort associated with general endoscopy. Capsule-type endoscopes may also obtain images of the small intestine, unable to be reached by general endoscopy.

Such capsule-type endoscopes, as described above, may include a camera capturing images of internal organs, a light source irradiating light to internal organs when images are captured, a wireless transmitter and an antenna, wirelessly transmitting the captured images to an image storage device on the exterior of the body, and a battery supplying power required to operate endoscopes, in a capsule having a size similar to that of a large pill.

When light is emitted from a light source to irradiate light to internal organs, a camera may capture images of internal organs. In general, a camera may capture one to three images per second. Wireless transmitters may modulate video signals, in order to wirelessly transmit captured images. Subsequently, modulated signals may be emitted as radio signals through an antenna to be transmitted to an image storage device disposed on the exterior of the body. Batteries may supply power required for the operation of cameras, light sources, and wireless transmitters.

Such a capsule-type endoscope according to the related art may only perform one-way communications. For example, such a capsule-type endoscope may only transmit captured images to an image storage device disposed on the exterior of the body.

However, there is requirement to observe states of organs in real time through images and to capture more detailed images in positions suspected to be abnormal. Since recently developed capsule-type endoscopes may control attitude, they may capture more images while staying in a specific position for longer. To this end, a control signal needs to be wirelessly transmitted from the exterior of the body to control a capsule-type endoscope, and the capsule-type endoscope needs to receive the transmitted control signal and perform a required function.

Radio waves may be used to wirelessly transmit a control signal to the capsule-type endoscope from the exterior of the body. However, living tissues constituting a human body include a large amount of water, and conductivity of the water reduces the magnitude of an electric field to attenuate a significant portion of transmitted radio waves. To receive the attenuated radio waves and restore the control signal, the capsule-type endoscope should amplify the received radio waves. A large amount of power is additionally consumed during such amplification.

Since a small size of the capsule-type endoscope causes the capacity of an embedded battery to be limited, the additional power consumption resulting from such amplification reduces an operating time of the capsule-type endoscope. Therefore, to improve a level of performance of the capsule-type endoscope, it is necessary to apply a wireless technology capable of significantly reducing consumed power while performing two-way (bidirectional) communications.

A technology, related to a capsule-type endoscope, is disclosed in, for example, Korean Patent Publication No. 10-2007-0018858 (entitled "MEDICAL WIRELESS CAPSULE-TYPE ENDOSCOPE SYSTEM", published on Feb. 14, 2007).

SUMMARY

An aspect of the present disclosure is to provide a capsule-type endoscope and a method of controlling the same. When the capsule-type endoscope receives a control signal, an amplification process may be omitted to reduce power consumption of the capsule-type endoscope and to increase an operating time of the capsule-type endoscope. In addition, miniaturization of the capsule-type endoscope may be achieved.

Example embodiments of the present disclosure provide a capsule-type endoscope including a battery, a camera configured to capture internal organ images, a light source configured to irradiate light to capture the internal organ images, and a light source driving power line supplying power, stored in the battery, to the light source. The light source driving power line is a loop antenna coil for reception of a control signal from an external coupled loop antenna coil for transmission.

Example embodiments of the present disclosure provide a method of controlling a capsule-type endoscope including a battery, a camera configured to capture internal organ images, a light source configured to irradiate light to capture the internal organ images, and a light source driving power line supplying power, stored in the battery, to the light source. The method includes receiving a control signal from an external coupled loop antenna coil for transmission by a loop antenna coil for reception, and controlling the capsule-type endoscope in response to the received control signal by a control circuit. The light source driving power line is used as the loop antenna coil for reception.

BRIEF DESCRIPTION OF DRAWINGS

The above and other aspects, features, and advantages of the present disclosure will be more clearly understood from the following detailed description when taken in conjunction with the accompanying drawings.

DETAILED DESCRIPTION

Example embodiments of the present disclosure will be described in detail with reference to the accompanying drawings. However, the present disclosure may be embodied in many different forms and should not be construed as limited to the embodiments set forth herein. Rather, these embodiments are provided so that the present disclosure will be thorough and complete, and will fully convey the scope of the present disclosure to those skilled in the art. In the drawings, the shapes and dimensions may be exaggerated for clarity, and the same reference signs are used to designate the same or similar components throughout.

Figure 1:
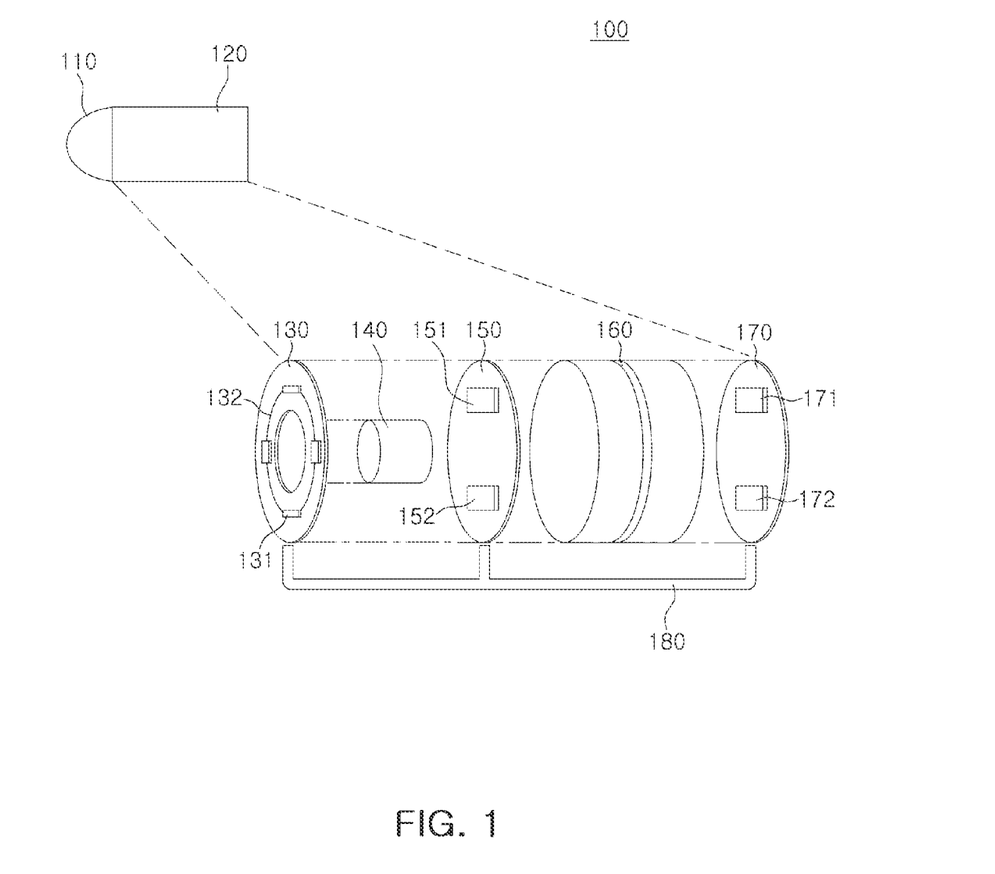
FIG. 1 is a view illustrating a capsule-type endoscope according to an example embodiment of the present disclosure.

FIG. 1 is a view illustrating a capsule-type endoscope 100 according to an example embodiment.

As illustrated in FIG. 1, the capsule-type endoscope 100 may include a transparent window 110 and a main body 120.

Specifically, the transparent window 110 may be formed of a transparent material to prevent light, emitted from a light source 131, and a field of view of a camera 140 from being blocked by the transparent window 110.

The main body 120 may include a light source substrate 130 on which a light source 131 such as a light emitting device (LED) and a light source driving power line 132 (the power line 132 being a loop antenna coil for reception of a control signal from an external coupled loop antenna coil for transmission), supplying power stored in a battery 160 to the light source 131, are formed, a camera 140 configured to capture internal organ images, an image processing substrate 150 on which an image processing circuit 151, configured to process the internal organ images captured by the camera 140, and a power supply circuit 152, configured to convert and supply the power stored in the battery 160, are mounted, the battery 160 configured to store power required to operate the capsule-type endoscope 100, a control substrate 170 on which a wireless transmission circuit 171, configured to wirelessly transmit the images processed by the image processing circuit 151, and a control circuit 172 configured to control the capsule-type endoscope 100 in response to the control signal received through the power line 132, are mounted, and a connection line 180 connecting the power supply circuit 152, a pad (to be described later) provided on the substrate 130, and the control circuit 172.

Figure 2:
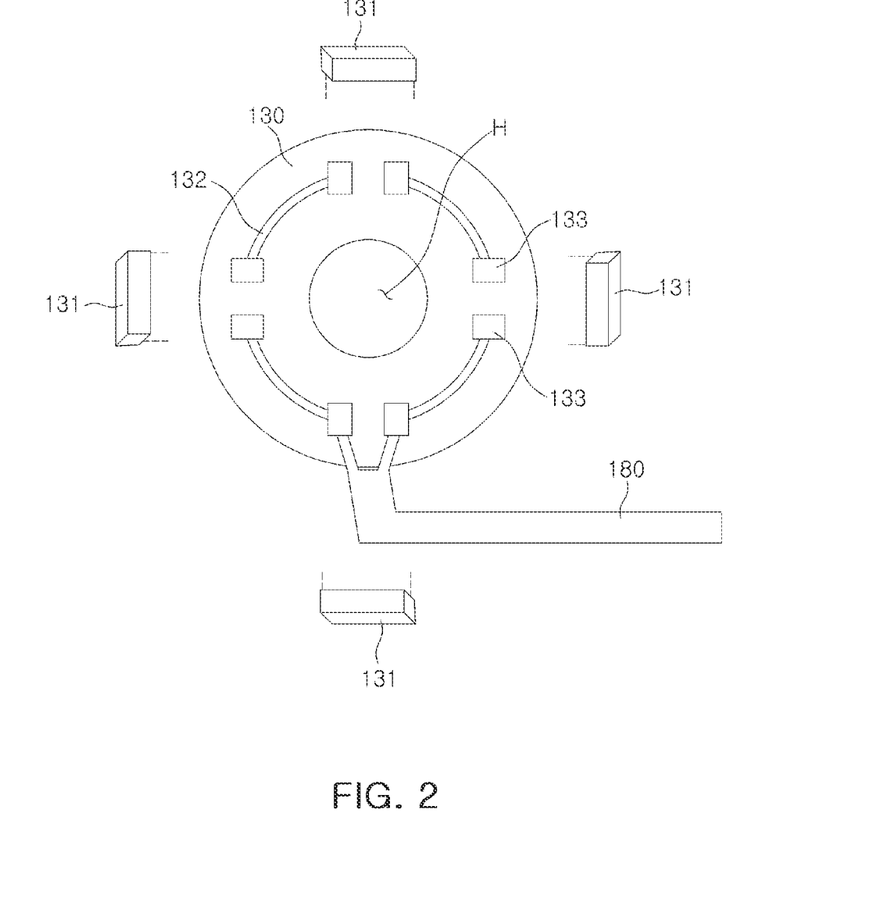
FIG. 2 is a view illustrating a light source driving power line, formed on a light source substrate according to an example embodiment of the present disclosure and serving as a loop antenna coil for reception of a control signal from an external coupled loop antenna for transmission while supplying power to the light source.

FIG. 2 is a view illustrating a light source driving power line 132, formed on a light source substrate according to an example embodiment of the present disclosure and serving as a loop antenna coil for reception of a control signal from an external coupled loop antenna for transmission while supplying power to the light source.

Hereinafter, the light source substrate 130, including the light source driving power line 132 according to an example embodiment of the present disclosure, will be described in detail with reference to FIG. 2. Although four light sources 131 and four pairs of pads 133 for the four light sources 131 are illustrated in FIG. 2, it will be apparent to those skilled in the art that the number of the light sources 131 and the number of the pads 133 may be changed, as necessary.

Referring to FIG. 2, a camera through-hole H, into which the camera 140 is inserted, may be formed in the center of the light source substrate 130. In addition, a pad 133 for mounting the light source 131 may be provided around the camera through-hole H.

According to an example embodiment, the above-described light source driving power line 132 may be a metal wire extending, in circular form, from the pad 133 on the light source substrate 130. Such a metal wire may serve as a loop coil antenna for reception (also, referred to as "reception coil") configured to receive a control signal from an external coupled loop antenna for transmission (also, referred to as "transmission coil"). The above-described control signal may be a modulated magnetic field signal of a high frequency band.

That is, according to an example embodiment, a loop antenna coil for transmission, not illustrated, may transmit a control signal, a modulated magnetic field signal of a high frequency band, and a loop antenna coil for reception may be coupled to the loop antenna coil for transmission to receive the control signal, a modulated magnetic field signal of a high frequency band, from the loop antenna coil for transmission. Therefore, unlike the related art in which a control signal is received using an existing radio wave, an amplification process may be omitted to reduce power consumption of the capsule-type endoscope and to increase an operating time of the capsule-type endoscope.

In addition, according to an example embodiment, alight source driving power line, supplying power to the light source 131, may be used as a loop antenna coil for reception. Therefore, since an additional space for a loop antenna coil for reception is not required, miniaturization of the capsule-type endoscope may be achieved.

Figure 3:
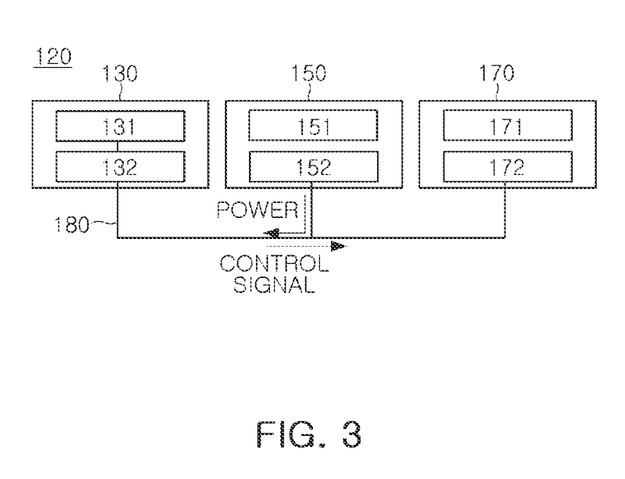
FIG. 3 is a view illustrating functional blocks of a capsule-type endoscope according to an example embodiment of the present disclosure.

FIG. 3 is a view illustrating functional blocks of the capsule-type endoscope according to an example embodiment of the present disclosure. In FIG. 3, the camera 140 and the battery 160 are not illustrated.

As illustrated in FIG. 3, the capsule type endoscope may include a light source substrate 130 including a light source 131 and a light source driving power line 132, an image processing substrate 150 on which an image processing circuit 151 and a power supply circuit 152 are mounted, a control substrate 170 on which a wireless transmission circuit 171 and a control circuit 172 are mounted, and a connection line 180.

According to an example embodiment, the power supply circuit 152 may include a radio-frequency (RF) choke, and the control circuit 172 may include a direct current (DC) block.

Specifically, the RF choke may be a module passing power of a battery, a DC signal, while blocking a control signal, a modulated magnetic field signal of a high frequency band.

For example, the power supply circuit 152 may convert DC power, stored in the battery 160, into DC power having an appropriate level and may supply the converted DC power to respective modules (a camera, a light source, a control circuit, and the like) of the capsule-type endoscope 100. In addition, it is necessary to prevent a radio-frequency signal from entering the power supply circuit 152.

Therefore, according to an example embodiment, the power supply circuit 152 may include an RF choke to block a modulated magnetic field signal of a high frequency band received through the light source driving power line 132.

The DC block may be a module blocking converted power of a battery, a DC signal, while passing a modulated magnetic field signal of a high frequency band.

For example, the control circuit 172 may control the capsule-type endoscope in response to the control signal received through the light source driving power line 132, and it is necessary to prevent DC power from reaching the control circuit 172.

Therefore, according to an example embodiment, the control circuit 172 may include a DC block to prevent DC power, a DC signal, from reaching the control circuit 172.

Figure 4:
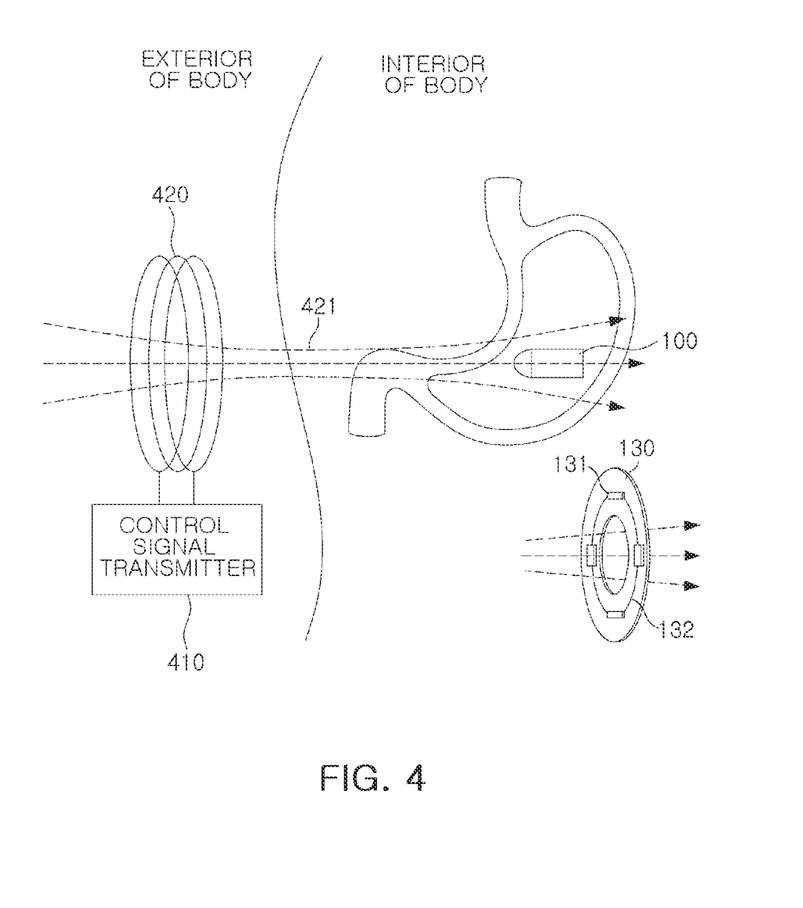
FIG. 4 is a view illustrating an operation of a capsule-type endoscope receiving the control signal from an external coupled loop antenna coil for transmission.

FIG. 4 is a view illustrating an operation of a capsule-type endoscope receiving the control signal from an external coupled loop antenna coil for transmission.

Hereinafter, an operation of a capsule-type endoscope 100 will be described with reference to FIG. 4.

A control signal transmitter 410 and a loop antenna coil 420 for transmission may be provided on an exterior of a body. The control signal transmitter 410 may generate a control signal. The generated control signal may be transmitted to a loop antenna coil 132 for reception, coupled to the loop antenna coil 420 for transmission, of the capsule-type endoscope 100. In this case, the control signal may be a modulated magnetic field signal of a high frequency band.

The loop antenna coil 132 for reception of the capsule-type endoscope may receive the control signal of the external coupled loop antenna coil 420 for transmission, and a control circuit 420 may control the capsule-type endoscope 100 in response to the received control signal. Since the control signal, received through the loop antenna coil 132 for reception, is a modulated magnetic field signal of a high frequency band, it is apparent to those skilled in the art that a control circuit 172 may further perform a demodulation process to demodulate the modulated magnetic field signal.

According to an example embodiment, as described above, the loop antenna coil 132 for reception may be a light source driving power line 132 supplying power, stored in a battery 160, to a light source 131.

According to an example embodiment, as described above, a power supply circuit 152 may include an RF choke to block the modulated magnetic field signal of a high frequency band, received through the light source driving power line 132, and the control circuit 172 may include a DC block to prevent DC power, a DC signal, from reaching the control circuit 172.

Figure 5:
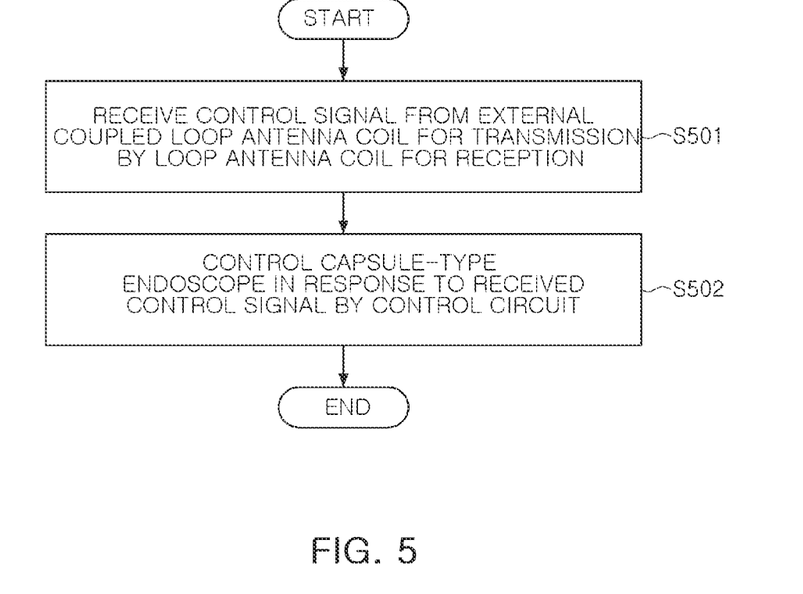
FIG. 5 is a flowchart illustrating a method of controlling a capsule-type endoscope according to an example embodiment of the present disclosure.

FIG. 5 is a flowchart illustrating a method of controlling a capsule-type endoscope according to an example embodiment of the present disclosure. Hereinafter, a method of controlling a capsule-type endoscope according to an example embodiment will be described with reference to FIGS. 1 to 5. For simplicity of description, duplicate descriptions with the matters described above with reference to FIGS. 1 to 4 will be omitted.

As illustrated in FIGS. 1 to 5, the loop antenna coil 132 for reception of the capsule-type endoscope 100 may receive a control signal from the external coupled loop antenna coil 420 for transmission (S501). The received control signal may be a modulated magnetic field signal of a high frequency band, and may be transmitted to the control circuit 172.

The control circuit 172 of the capsule-type endoscope 100 may control the capsule-type endoscope 100 in response to the received control signal (S502).

According to an example embodiment, as described above, the loop antenna coil 132 for reception may be a light source driving power line 132 supplying power, stored in the battery 160, to the light source 131.

According to an example embodiment, as described above, the power supply circuit 152 may include an RF choke to block a modulated magnetic field signal of a high frequency band received through the light source driving power line 132, and the control circuit 172 may include a DC block to prevent DC power, a DC signal, from reaching the control circuit 172.

According to an example embodiment, as described above, a light source driving power line may be used as a loop antenna coil for reception supplying power, stored in a battery, to a light source and simultaneously receives a control signal from an external coupled loop antenna coil for transmission. Thus, when receiving the control signal, an amplification process may be omitted to reduce power consumption of the capsule-type endoscope and to increase an operating time of the capsule-type endoscope.

As described so far, a light source driving power line, supplying power stored in a battery to a light source, may be used as a loop antenna coil for reception of a control signal, a modulated magnetic field signal of a high frequency band, from an external coupled loop antenna coil for transmission. Thus, when receiving a control signal, an amplification process may be omitted to reduce power consumption of a capsule-type endoscope, to increase an operating time of the capsule-type endoscope, and to achieve miniaturization of the capsule-type endoscope.

While specific examples have been illustrated and described above, it will be apparent after gaining an understanding of this disclosure that various changes in form and details may be made in these examples without departing from the spirit and scope of the claims and their equivalents. The examples described herein are to be considered in a descriptive sense only, and are not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:
1. A capture-type endoscope comprising:
   a battery;
   a camera configured to capture internal organ images;
   a light source configured to irradiate light to capture the internal organ images;

a light source driving power line supplying power, stored in the battery, to the light source; and a power supply circuit configured to convert and supply power of the battery, wherein the light source driving power line is a loop antenna coil for reception of a control signal from an external coupled loop antenna coil for transmission, the control signal is a modulated magnetic field signal of a high frequency band, and the power supply circuit comprises:

a radio-frequency (RF) choke configured to pass the converted power of the battery, a direct current (DC) signal, but to block the modulated magnetic field signal of a high frequency band.

2. The capsule-type endoscope of claim 1, further comprising:

a light source substrate provided with a pad for mounting the light source, wherein the light source driving power line is a metal wire extending, in circular form, from the pad on the light source substrate.

3. The capsule-type endoscope of claim 2, further comprising:

a control circuit configured to control the capsule-type endoscope in response to the received control signal; and a connection line connecting the power circuit, the pad provided on the light source substrate, and the control circuit to each other.

4. The capsule-type endoscope of claim 3, wherein the control circuit comprises:

a DC block configured to block the converted power of the battery, a direct current (DC) signal, but to pass the modulated magnetic field signal of a high frequency band.

5. A method of controlling a capsule-type endoscope comprising a battery, a camera configured to capture internal organ images, a light source configured to irradiate light to capture the internal organ images, light source driving power line supplying power, stored in the battery, to the light source, and a power supply circuit configured to convert and supply power of the battery, the method comprising:

receiving a control signal from an external coupled loop antenna coil for transmission by a loop antenna coil for reception; and controlling the capsule-type endoscope in response to the received control signal by a control circuit, wherein the light source driving power line is used as the loop antenna coil for reception, the control signal is a modulated magnetic field signal of a high frequency band, and the power supply circuit comprises:

a radio-frequency (RF) choke configured to pass the converted power of the battery, a direct current (DC) signal, but to block the modulated magnetic field signal of a high frequency band.

* * * * *